United States Patent
Overstreet

(10) Patent No.: US 7,117,038 B1
(45) Date of Patent: Oct. 3, 2006

(54) METHOD AND SYSTEM FOR OBTAINING STAPEDIAL REFLEXES IN COCHLEAR IMPLANT USERS USING MULTIBAND STIMULI

(75) Inventor: Edward H Overstreet, Stevenson Ranch, CA (US)

(73) Assignee: Advanced Bionics Corporation, Valencia, CA (US)

( * ) Notice: Subject to any disclaimer, the term of this patent is extended or adjusted under 35 U.S.C. 154(b) by 52 days.

(21) Appl. No.: 10/662,615

(22) Filed: Sep. 15, 2003

Related U.S. Application Data

(60) Provisional application No. 60/412,533, filed on Sep. 20, 2002.

(51) Int. Cl.
*A61B 1/10* (2006.01)

(52) U.S. Cl. ....................................... 607/57
(58) Field of Classification Search ............... 607/5, 607/57, 56; 600/25
See application file for complete search history.

(56) References Cited

U.S. PATENT DOCUMENTS

| | | | |
|---|---|---|---|
| 3,751,605 | A | 8/1973 | Michelson |
| 4,400,590 | A | 8/1983 | Michelson |
| 5,626,629 | A | 5/1997 | Faltys et al. |
| 5,938,691 | A | 8/1999 | Schulman et al. |
| 6,067,474 | A | 5/2000 | Schulman et al. |
| 6,157,861 | A | 12/2000 | Faltys et al. |
| 6,195,585 | B1 | 2/2001 | Karunasiri et al. |
| 6,205,360 | B1 | 3/2001 | Carter et al. |
| 6,208,882 | B1 | 3/2001 | Lenarz et al. |
| 6,219,580 | B1 | 4/2001 | Faltys et al. |
| 6,249,704 | B1 | 6/2001 | Maltan et al. |
| 6,289,247 | B1 | 9/2001 | Faltys et al. |
| 6,295,467 | B1 | 9/2001 | Kollmeier et al. |
| 6,415,185 | B1 | 7/2002 | Maltan |

OTHER PUBLICATIONS

Overstreet, et al. inventors for AB-254U; U.S. Appl. No. 10/218,645; filed Aug. 13, 2002; entitled "Cochlear Implant and Simplified Method of Fitting".

Segel, et al. inventors for AB-313U; U.S. Appl. No. 10/651,653; filed Aug. 29, 2003; entitled "System and Method for Fitting a Cochlear Implant Sound Processor Using Alternative Signals".

*Primary Examiner*—George Manuel
(74) *Attorney, Agent, or Firm*—Bryant R. Gold

(57) ABSTRACT

A method and system for fitting a multichannel cochlear implant system to a patient increases the percentage of patients for which stapedial reflexes can be obtained, and increases the accuracy of predicting the "live speech" comfort levels of the patient's fitting programs from the stapedial reflex. Electrical stimuli are applied on multiple electrodes at "live speech" pulse rates. The neural excitation patterns elicited from such stimulation more closely resemble that which occurs when the system is subjected to normal speech patterns. By progressively setting threshold levels in bands, e.g., groups of electrodes, either overlapping or non-overlapping, as well as with a final check by globally adjusting the band obtained contour to the stapedial reflex, such values more closely resemble actual "live speech" program levels than those obtained with traditional methods. Further, broader excitation patterns produced by the activation of multiple electrodes increases the probability of obtaining reflex measurements where single electrode stimulation fails due to sparse neural survival.

20 Claims, 6 Drawing Sheets

METHOD AND SYSTEM FOR OBTAINING STAPEDIAL REFLEXES IN COCHLEAR IMPLANT USERS USING MULTIBAND STIMULI

The present application claims the benefit of U.S. Provisional Patent Application Ser. No. 60/412,533, filed Sep. 20, 2002, which application is incorporated herein by reference.

BACKGROUND OF THE INVENTION

The present invention relates to cochlear implants, and more particularly to a method for sensing, measuring and using the stapedial reflex in a cochlear implant through the use of multiband stimuli.

Electrical stimulation of predetermined locations within the cochlea of the human ear through an intra-cochlear electrode array is described, e.g., in U.S. Pat. No. 4,400,590. The electrode array shown in the '590 patent comprises a plurality of exposed electrode pairs spaced along and imbedded in a resilient curved base for implantation in accordance with a method of surgical implantation, e.g., as described in U.S. Pat. No. 3,751,615. The system described in the '590 patent receives audio signals, i.e., sound waves, at a signal processor (or speech processor) located outside the body of a hearing impaired patient. The speech processor converts the received audio signals into modulated RF data signals that are transmitted by a cable connection through the patient's skin to an implanted multi-channel intracochlear electrode array. The modulated RF signals are demodulated into analog signals and are applied to selected ones of the plurality of exposed electrode pairs in the intra-cochlear electrode so as to electrically stimulate predetermined locations of the auditory nerve within the cochlea.

U.S. Pat. No. 5,938,691, incorporated herein by reference, shows an improved multi-channel cochlear stimulation system employing an implanted cochlear stimulator (ICS) and an externally wearable speech processor (SP). The speech processor employs a headpiece that is placed adjacent to the ear of the patient, which receives audio signals and transmits the audio signals back to the speech processor. The speech processor receives and processes the audio signals and generates data indicative of the audio signals for transcutaneous transmission to the implantable cochlear stimulator. The implantable cochlear stimulator receives the transmission from the speech processor and applies stimulation signals to a plurality of cochlea stimulating channels, each having a pair of electrodes in an electrode array associated therewith. Each of the cochlea stimulating channels uses a capacitor to couple the electrodes of the electrode array.

Other improved features of a cochlear implant system are taught, e.g., in U.S. Pat. Nos. 5,626,629; 6,067,474; 6,157,861; 6,195,585; 6,205,360; 6,219,580; 6,249,704; 6,289,247; 6,295,467; and 6,415,185; each of which patents is incorporated herein by reference.

The implantable cochlear stimulators described in the U.S. Pat. Nos. 5,626,629; 6,067,474; 6,157,861 and 6,219,580 are also able to selectively control the pulse width of stimulating pulses that are applied through the electrode array to the cochlea, and the frequency at which the stimulating pulses are applied.

The implantable cochlear stimulators described in the U.S. Pat. Nos. 6,157,861 and 6,195,585 teach the use of the stapedius reflex (also referred to as the stapedial reflex) as a parameter for monitoring and adjusting the magnitude of the stimuli applied through the electrode array.

A new generation of cochlear implants, sometimes referred to as "bionic ear" implants, have enhanced processing power, and can provide multiple platforms for delivering electrical stimuli to the auditory nerve. Such electrical stimuli includes high frequency pulsitile stimulation having current pulses of controlled amplitude, width and frequency.

As the art of cochlear stimulation has advanced to produce bionic ear implants, the implanted portion of the cochlear stimulation system, and the externally wearable processor (or speech processor) have become increasingly complicated and sophisticated. It is also noted that much of the circuitry previously employed in the externally wearable processor has been moved to the implanted portion, thereby reducing the amount of information that must be transmitted from the external wearable processor to the implanted portion. The amount of control and discretion exercisable by an audiologist in selecting the modes and methods of operation of the cochlear stimulation system have increased dramatically and it is no longer possible to fully control and customize the operation of the cochlear stimulation system through the use of, for example, switches located on the speech processor. As a result, it has become necessary to utilize an implantable cochlear stimulator fitting system to establish the operating modes and methods of the cochlear stimulation system and then to download such programming into the speech processor. One such fitting system is described in the U.S. Pat. No. 5,626,629. Another fitting system is described in the U.S. Pat. No. 6,289,247.

The U.S. Pat. No. 6,289,247 further highlights representative stimulation strategies that may be employed by a multichannel stimulation system. Such strategies represent the manner or technique in which the stimulation current is applied to the electrodes of an electrode array used with the stimulation system. Such stimulation strategies, all of which apply current pulses to selected electrodes, may be broadly classified as: (1) sequential or non-simultaneous (where only one electrode receives a current pulse at the same time); (2) simultaneous (where substantially all of the electrodes receive current stimuli at the same time, thereby approximating an analog signal); or (3) partially simultaneous pulsitile stimulation (where only a select grouping of the electrodes receive stimuli at the same time in accordance with a predefined pattern).

Typically, when the fitting systems described in the U.S. Pat. No. 5,626,629 or U.S. Pat. No. 6,289,247 are employed for multichannel stimulation systems, or when equivalent or similar fitting systems are employed, it is necessary to use directly measured threshold values and/or thresholds derived from the measurement of psycophysically-determined pseudo-comfort levels. That is, for each channel of the multichannel system, a minimum threshold level is measured, typically referred to as a "T" level, which represents the minium stimulation current which when applied to a given electrode associated with the channel produces a sensed perception of sound at least 50% of the time. In a similar manner, an "M" level is determined for each channel, which represents a stimulation current which when applied to the given electrode produces a sensed perception of sound that is moderately loud, or comfortably loud, but not so loud that the perceived sound is uncomfortable. These "T" and "M" levels are then used by the fitting software in order to properly map sensed sound to stimulation current levels that can be perceived by the patient as sound.

Disadvantageously, determining the "T" and/or "M" levels (or other required thresholds) associated with each channel of a multichannel stimulation system is an extremely painstaking and time-intensive task. Such determinations require significant time commitments on the part of the clinician, as well as the patient. Moreover, once determined one channel at a time, such levels may not be representative of actual threshold levels that are present during real speech. That is, preliminary data indicate that thresholds set in single channel psychophysics overestimate the actual threshold required when all channels are running during live speech. Such an overestimation appears to penalize patient performance, particularly performance in noise. Hence, neural stimulation parameters which render threshold measurement unnecessary would dramatically reduce the time requirements for programming sequential and/or partially simultaneous pulsitile stimulation, as well as facilitate a higher probability of optimized programming for pediatric as well as adult populations where obtaining such measures are difficult.

As the ages of patients into which implantable cochlear stimulators are implanted decreases, it becomes increasingly more important to improve the fitting process and to minimize, or eliminate, the need to make threshold measurements. This is because very young patients, for example, two year olds, are unable to provide adequate subjective feedback to the audiologist for the audiologist to accurately "fit" the cochlear stimulation system optimally for the patient. Thus, what is needed is an improved apparatus and simplified method for fitting a speech processor where many of the threshold measurements previously required are no longer needed, or where subjective feedback from the patient is no longer needed.

One technique that has been investigated for improving the manner in which threshold measurements are made or used is to sense the stapedius reflex of the patient in response to an applied stimulus. See, e.g., the U.S. Pat. Nos. 6,157,861 and 6,195,585, previously incorporated herein by reference. An electrode that may be used to sense the stapedius reflex is described, e.g., in U.S. Pat. No. 6,208,882, also incorporated herein by reference.

When the stapedius reflex is sensed, i.e., when a stapedius reflex electrode is in place that allows the stapedius reflex to be sensed, or when other techniques are used to sense the stapedius reflex, such sensing eliminates or minimizes the need to rely solely upon subjective feedback from the patient during the fitting or adjusting process. Such subjective feedback can be highly unreliable, particularly in younger and older patients.

Traditional methods for measuring stapedial reflexes present stimuli, typically pulse trains, on a single electrode and the reflex is either directly observed by visual inspection or is inferred from a change in the impedance of the tympanic membrane. Advantageously, when compared to other objective measures such as neural responses in the cochlea or brainstem, the stapedial reflex shows the strongest correlation to the patient's comfort level to the stimulus. In spite of this correlation to comfort level, which has primarily utility for the programming of implants in children, there are two major problems that limit is effectiveness as a clinical tool. These problems are: (1) approximately 20–30% of patients do not provide an easily measured stapedial reflex, and (2) single electrode measurements fail to account for temporal and spatial integration, and thus such single electrode measurements likewise fail to account for the actual comfort level settings for the stimulus during multi-electrode activation, as occurs during "live speech".

It is thus seen that improvements are still needed in the manner in which the stapedial reflex is obtained and used during the fitting and operation of a cochlear implant system.

SUMMARY OF THE INVENTION

The present invention addresses the above and other needs by (1) increasing the percentage of patients for which stapedial reflexes can be obtained, and (2) increasing the accuracy of predicting the "live speech" comfort levels of the patient's fitting programs from the stapedial reflex.

The present invention is intended for use with multichannel cochlear stimulation systems, i.e., cochlear stimulation systems wherein stimuli can be applied simultaneously to multiple channels, or can be applied sequentially to multiple channels at a sufficiently fast rate so that the stimuli are perceived as having been applied simultaneously.

In accordance with one aspect of the invention, electrical stimuli are applied on multiple electrodes at "live speech" pulse rates, e.g., pulse rates equal to or greater than about 2 KHz. The magnitude, or amplitude, of the electrical stimuli may be modulated or unmodulated, but is preferably modulated. When modulated, a peak, RMS, average, mean, or other measure of the applied modulated stimuli may be used to track and control the energy level of the applied stimuli. When stimuli are applied on multiple electrodes at such "live speech" rates, the neural excitation patterns more closely resemble that which occurs during normal program operation, i.e., when the system is subjected to normal speech patterns. The advantages of using such modulated electrical stimuli are more fully described in co-pending application Ser. No. 10/651,653, filed Aug. 29, 2003 and Ser. No. 10/218,645, filed Aug. 13, 2002, each of which applications is assigned to the same assignee as is the present application and each of which application is incorporated herein by reference in its entirety, including any Appendices that form a part thereof.

Advantageously, when electrical stimuli are applied on multiple electrodes at "live speech" pulse rates, the level at which the stapedial reflex is elicited shows a higher correlation with actual "live speech" comfort levels.

Hence, in accordance with another aspect of the invention, stimulus levels are progressively set in bands, e.g., groups of electrodes or channels. By progressively setting threshold levels in bands, either overlapping or non-overlapping, as well as with a final check by globally adjusting the band obtained contour to the stapedial reflex, such values more closely resemble actual "live speech" program levels than those obtained with traditional methods, i.e., unmodulated pulse trains presented on single electrodes. Further, broader excitation patterns produced by the activation of multiple electrodes increases the probability of obtaining reflex measurements where single electrode stimulation fails due to sparse neural survival.

It is thus a feature of the present invention to provide an improved method of fitting a multichannel cochlear implant system that uses the stapedial reflex of the patient and multiband stimulation to better determine effective intensity threshold levels, e.g., T and M levels, used by the implant system during its operation.

It is a further feature of the invention to provide such an improved method of fitting that does not require subjective feedback from the patient during the fitting procedure.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
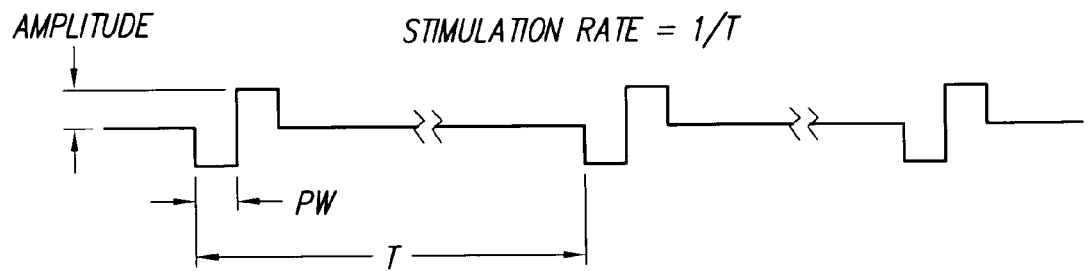
FIG. 1 is a current stimulation waveform that defines the stimulation rate (1/T) and biphasic pulse width (PW) associated with electrical stimuli.

FIG. 1 shows a waveform diagram of a biphasic pulse train, and defines stimulation rate, pulse width and pulse amplitude.

Figure 2A:
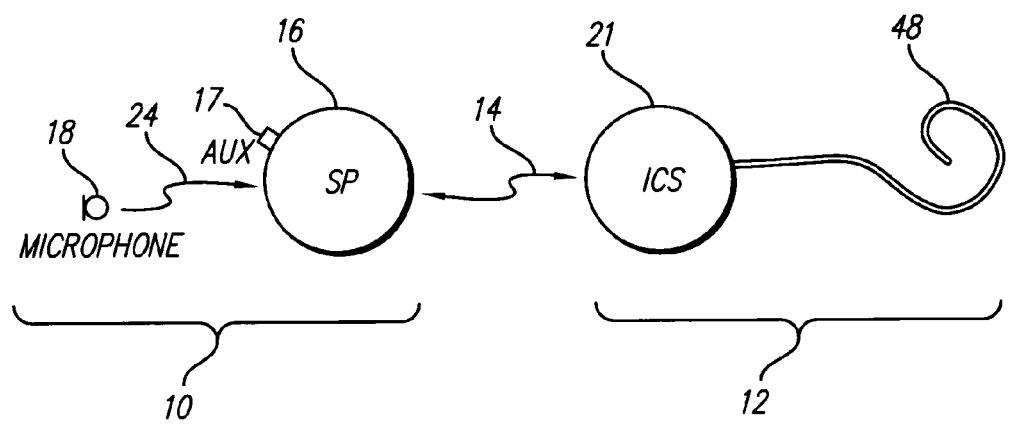
FIGS. 2A and 2B respectively show a cochlear implant system and a partial functional block diagram of the cochlear stimulation system, which system is capable of providing high rate pulsitile electrical stimuli on multiple channels.

FIG. 2A shows a cochlear stimulation system that includes a speech processor portion 10 and a cochlear stimulation portion 12. The speech processor portion 10 includes a speech processor (SP) 16 and a microphone 18. The microphone 18 may be connected directly to the SP 16, or may be coupled to the SP 16 through an appropriate communication link 24. An auxiliary input port 17 may also be part of the speech processor 16 to allow input signals from a source other than the microphone 18 to be input into the SP 16.

The cochlear stimulation portion 12 includes an implantable cochlear stimulator (ICS) 21 and an electrode array 48. The electrode array 48 is adapted to be inserted within the cochlea of a patient. The array 48 includes a multiplicity of electrodes, e.g., sixteen electrodes, spaced along its length that are selectively connected to the ICS 21. The electrode array 48 may be substantially as shown and described in U.S. Pat. No. 4,819,647 or U.S. Pat. No. 6,129,753, incorporated herein by reference. Electronic circuitry within the ICS 21 allows a specified stimulation current to be applied to selected pairs or groups of the individual electrodes included within the electrode array 48 in accordance with a specified stimulation pattern, defined by the SP 16.

The ICS 21 and the SP 16 are shown in FIG. 2A as being linked together electronically through a suitable data or communications link 14. In some cochlear implant systems, the SP 16, auxiliary input port 17 and microphone 18 comprise the external portion of the cochlear implant system; and the ICS 21 and electrode array 48 comprise the implantable portion of the system. Thus, the data link 14 is a transcutaneous data link that allows power and control signals to be sent from the SP 16 to the ICS 21. In some embodiments, data and status signals may also be sent from the ICS 21 to the SP 16.

In recent cochlear implant systems, as shown more particularly below in FIG. 2B, at least certain portions of the SP 16 are included within the implantable portion of the overall cochlear implant system, while other portions of the SP 16 remain in the external portion of the system. In general, at least the microphone 18 (and auxiliary input port 17, if used) and associated analog front end (AFE) circuitry 22 will be part of the external portion of the system; and at least the ICS 21 and electrode array 48 are part of the implantable portion of the invention. As used herein, "external" means not implanted under the skin or residing within the inner ear. However, "external" may mean within the outer ear, including in the ear canal, and may also include within the middle ear.

Typically, where a transcutaneous data link must be established between the external portion and implantable portions of the system, such link is realized by an internal antenna coil within the implantable portion, and an external antenna coil within the external portion. In use, the external antenna coil is positioned so as to be aligned over the location where the internal antenna coil is implanted, allowing such coils to be inductively coupled to each other, thereby allowing data (e.g., the magnitude and polarity of a sensed acoustic signals) and power to be readily transmitted from the external portion to the implantable portion. Note, in other embodiments of the invention, both the SP 16 and the ICS 21 may be implanted within the patient, either in the same housing or in separate housings. If in the same housing, the link 14 may be realized with a direct wire connection within such housing. If in separate housings, as taught, e.g., in U.S. Pat. No. 6,067,474, incorporated herein by reference, the link 14 may be an inductive link using a coil or a wire loop coupled to the respective parts.

The microphone 18 senses acoustic signals and converts such sensed signals to corresponding electrical signals, and may thus be considered as an acoustic transducer. The electrical signals are sent to the SP 16 over a suitable electrical or other link 24. Alternatively, electrical signals may be input directly into the auxiliary input port 17 from a suitable signal source. Still alternatively, the electrical signals may be generated within the speech processor and applied directly to the processing signal paths utilized within the speech processor, thereby effectively bypassing the front end circuitry of the speech processor. Such bypassed front end circuitry may include the microphone 18, the AFE circuitry 22, the A/D circuitry 28 and/or the AGC circuitry 29.

The SP 16 processes the converted acoustic signals received from the microphone 18, or the electrical signals received through the auxiliary input port 17, or the electrical signals generated internally within the speech processor, in accordance with a selected speech processing strategy in order to generate appropriate control signals for controlling the ICS 21. In operation, such control signals specify or define the polarity, magnitude, location (which electrode pair or other group of electrodes receives the stimulation current), and timing (when the stimulation current is applied to the electrode pair or other group) of the stimulation current that is generated by the ICS. Such control signals thus combine to produce a desired spatiotemporal pattern of electrical stimuli in accordance with the desired speech processing strategy. Unlike early cochlear implant systems, more modern cochlear implant systems advantageously confine such control signals to circuitry within the implantable portion of the system, thereby avoiding the need to continually send or transmit such control signals across a transcutaneous link.

The speech processing strategy is used, inter alia, to condition the magnitude and polarity of the stimulation current applied to the implanted electrodes of the electrode array 48. Such speech processing strategy involves defining a pattern of stimulation waveforms that are to be applied to the electrodes as controlled electrical currents. In accordance with the present invention, during the fitting process, a strategy is used which stimulates selected groups of the implanted electrodes with a high rate pulsitile pattern that is amplitude modulated by sound information. During such stimulation, the stapedial reflex of the patient is monitored for a desired reflex criteria. The types of stimulation patterns applied to the electrode groups may be conveniently categorized as: (1) simultaneous stimulation patterns, or (2) non-simultaneous stimulation patterns. Simultaneous stimulation patterns may be "fully" simultaneous or partially simultaneous. A fully simultaneous stimulation pattern is one wherein stimulation currents, either analog or pulsitile, are applied to the electrodes of all of the available channels at the same time. A partially simultaneous stimulation pattern is one wherein stimulation currents, either analog or pulsitile, are applied to the electrodes of two or more channels, but not necessarily all of the channels, at the same time. Examples of each type are strategy given in U.S. Pat. No. 6,289,247, incorporated herein by reference. A non-simultaneous stimulation pattern applies stimulation currents to electrodes in a sequential manner, e.g., only one electrode pair at a time. However, the rate of stimulation applied to different electrode pairs may be sufficiently fast so that the stimulation is perceived by the patient as though it were applied to all of the selected electrode pairs simultaneously.

Analog waveforms used in analog stimulation patterns are typically reconstructed by the generation of continuous short monophasic pulses (samples). The sampling rate is selected to be fast enough to allow for proper reconstruction of the temporal details of the signal. An example of such a sampled analog stimulation pattern is a simultaneous analog sampler (SAS) strategy.

Current pulses applied in pulsitile stimulation patterns are generally biphasic pulses, as shown in FIG. 1, but may also be multiphasic pulses, applied to the electrodes of each channel. The biphasic/multiphasic pulse has a magnitude (e.g., amplitude and/or duration) that varies as a function of the sensed acoustic signal or other source of modulation. (A "biphasic" pulse is generally considered as two pulses: a first pulse of one polarity having a specified magnitude, followed immediately, or after a very short delay, by a second pulse of the opposite polarity having the same total charge, which charge is the product of stimulus current times duration of each pulse or phase.) For multichannel cochlear stimulators of the type used with the present invention, it is common to apply a high rate biphasic stimulation pulse train to each of the pairs of electrodes in a selected group of electrodes in accordance with a selected strategy, and modulate the pulse amplitude of the pulse train as a function of information contained within the sensed acoustic signal, or the received auxiliary input signal, or the internally generated input signal.

Figure 2B:
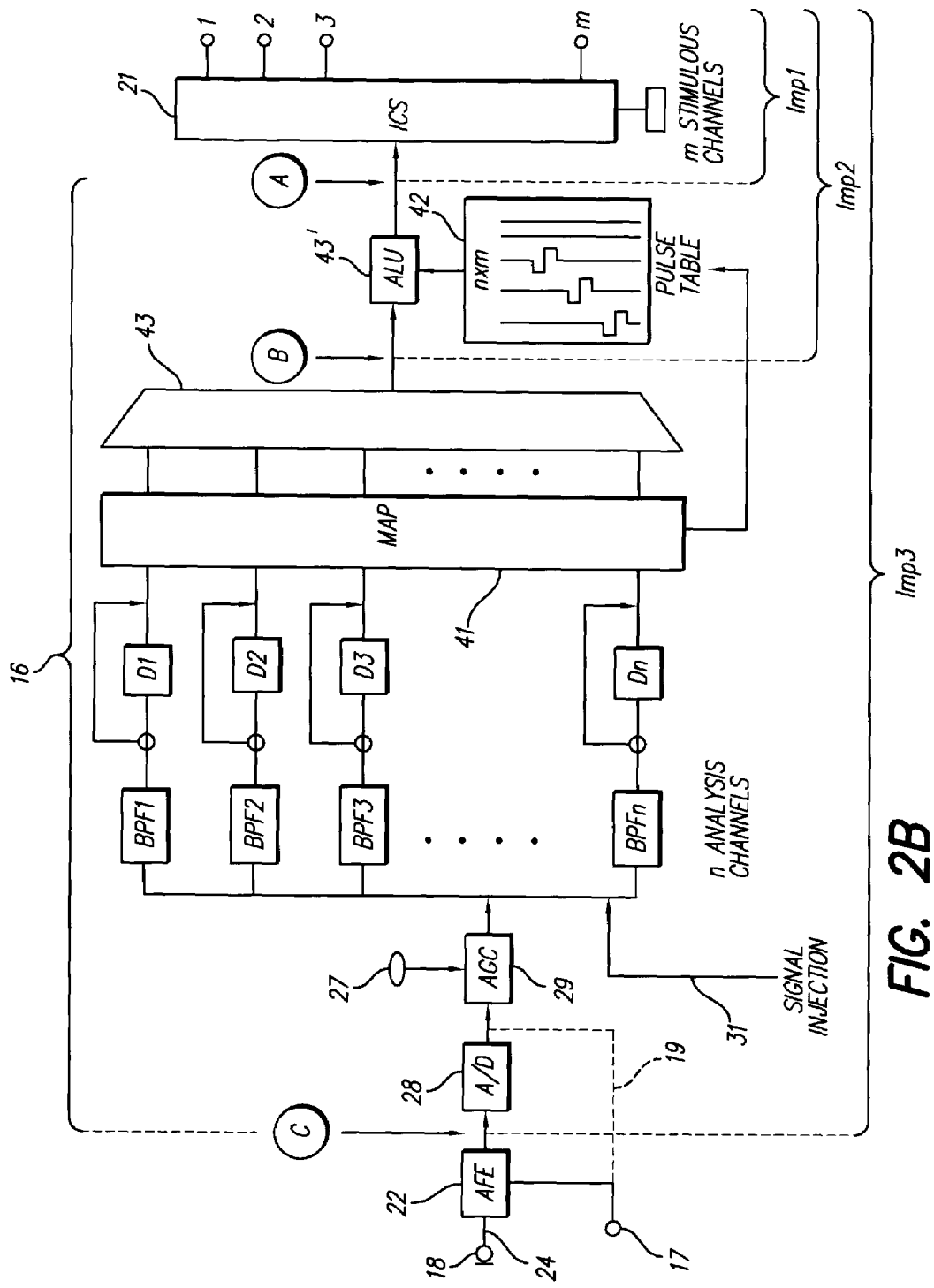

Turning next to FIG. 2B, a partial block diagram of a representative cochlear implant is shown. More particularly, FIG. 2B shows a partial functional block diagram of the SP 16 and the ICS 21 of an exemplary cochlear implant system capable of providing a high rate pulsitile stimulation pattern. That which is shown in FIG. 2B depicts the functions that are carried out by the SP 16 and the ICS 21. The actual electronic circuitry that is used to carry out these functions is not critical to understanding and practicing the present invention. It should also be pointed out that the particular functions shown in FIG. 2B are representative of just one type of signal processing strategy that may be employed (which divides the incoming signal into frequency bands, and independently processes each band). Other signal processing strategies could just as easily be used to process the incoming acoustical signal.

A complete description of the functional block diagram of the cochlear implant system shown in FIG. 2B is found in U.S. Pat. No. 6,219,580, incorporated herein by reference. It is to be emphasized that the functionality shown in FIG. 2B is only representative of one type of exemplary cochlear implant system, and is not intended to be limiting. The details associated with a given cochlear implant system are not critical to understanding and practicing the present invention.

In the manner described in the U.S. Pat. No. 6,219,580, the cochlear implant functionally shown in FIG. 2B provides n analysis channels that may be mapped to one or more stimulus channels. That is, as seen in FIG. 2B, after the incoming sound signal is received through the microphone 18 or auxiliary input port 17, and processed by the analog front end circuitry (AFE) 22, it is digitized in an analog to digital (A/D) converter 28, and then subjected to appropriate gain control (which may include compression) in an automatic gain control (AGC) unit 29. It should be noted that in some instances the signal input into the auxiliary input port 17 may already be digitized, in which case a signal path 19 is provided that bypasses the A/D converter 28. It should also be noted that in some instances an internally-generated signal, already digitized to have a correct gain, may be interjected directly into the signal processing path through a signal injection line 31.

After appropriate gain control, when needed, the signal is divided into n analysis channels, each of which includes a bandpass filter, $BPF_n$, centered at a selected frequency. The signal present in each analysis channel is processed as described more fully in the U.S. Pat. No. 6,219,580, and the signals from each analysis channel are then mapped, using mapping function 41, so that an appropriate stimulus current, of a desired amplitude and timing, may be applied through a selected stimulus channel to stimulate the auditory nerve.

Thus it is seen that the system of FIG. 2B provides a multiplicity of channels, n, wherein the incoming signal is processed and analyzed. The information contained in these n "analysis channels" is then appropriately processed, compressed and mapped in order to control the actual stimulus patterns that are applied to the patient by the ICS 21 and its associated electrode array 48. The electrode array 48 includes a multiplicity of electrode contacts, connected through appropriate conductors, to respective current generators, or pulse generators, within the ICS. Through these multiplicity of electrode contacts, a multiplicity of stimulus channels, e.g., m stimulus channels, exist through which individual electrical stimuli may be applied at m different stimulation sites within the patient's cochlea.

While it is common to use a one-to-one mapping scheme between the analysis channels and the stimulus channels, wherein n=m, and the signal analyzed in the first analysis channel is mapped to produce a stimulation current at the first stimulation channel, and so on, it is not necessary to do so. Rather, in some instances, a different mapping scheme may prove beneficial to the patient. For example, assume that n is not equal to m (n, for example, could be at least 20 or as high as 32, while m may be no greater than sixteen, e.g., 8 to 16). The signal resulting from analysis in the first analysis channel may be mapped, using appropriate mapping circuitry 41 or equivalent, to the first stimulation channel via a first map link, resulting in a first stimulation site (or first area of neural excitation). Similarly, the signal resulting from analysis in the second analysis channel of the SP may be mapped to the second stimulation channel via a second map link, resulting in a second stimulation site. Also, the signal resulting from analysis in the second analysis channel may be jointly mapped to the first and second stimulation channels via a joint map link. This joint link results in a stimulation site that is somewhere in between the first and second stimulation sites. The "in between site" is sometimes referred to as a virtual stimulation site. Advantageously, this possibility of using different mapping schemes between n SP analysis channels and m ICS stimulation channels to thereby produce a large number of virtual and other stimulation sites provides a great deal of flexibility with respect to positioning the neural excitation areas in a location that proves most beneficial to the patient.

Still with reference to FIG. 2B, it should be noted that the speech processing circuitry 16 generally includes all of the circuitry from point (C) to point (A). In some cochlear implant systems, the entire SP circuitry is housed in a speech processor that is part of the external (or non-implanted) portion of the system. That is, in such systems, only the ICS 21, and its associated electrode array, are implanted, as indicated by the bracket labeled "Imp1" (for "Implant-1"). This means that in such systems, the signal passing through the serial data stream at point (A) is also the signal that must pass through the transcutaneous communication link from the external unit to the implanted unit. Because such signal contains all of the defining control data for the selected speech processing strategy, for all m stimulation channels, it therefore has a fairly high data rate associated therewith. As a result of such high data rate, either the system operation must be slowed down, which is generally not desirable, or the bandwidth of the link must be increased, which is also not desirable because the operating power increases.

In contrast to Implant-1 systems, other cochlear implant systems, such as the CII Bionic Ear system or the HiRes90K system manufactured by Advanced Bionics Corporation of Sylmar, Calif., advantageously puts at least a portion of the speech processor 16 within the implanted portion of the system. For example, a cochlear implant system may place the Pulse Table 42 and arithmetic logic unit (ALU) 43 inside of the implanted portion, as indicated by the bracket labeled "Imp2" in FIG. 2B. Such partitioning of the speech processor 16 offers the advantage of reducing the data rate that must be passed from the external portion of the system to the implanted portion. That is, the data stream that must be passed to the implanted portion Imp2 comprises the signal stream at point (B). This signal is essentially the digitized equivalent of the modulation data associated with each of the n analysis channels, and (depending upon the number of analysis channels and the sampling rate associated with each) may be significantly lower than the data rate associated with the signal that passes through point (A). Hence, improved performance without sacrificing power consumption may be obtained with a bionic ear implant of the type illustrated in FIG. 2B.

Other cochlear implant systems under development will incorporate more and more of the speech processor 16 within the implanted portion of the system. For example, a fully implanted speech processor 16 incorporates all of the SP in the implanted portion, as indicated by the bracket labeled Imp3 in FIG. 2B. Such a fully implanted speech processor offers the advantage that the data input into the system, i.e., the data stream that passes through point (C), need only have a rate commensurate with the input signal received through the microphone 18 or the auxiliary input port 17.

With the preceding as background information relative to a typical cochlear implant system, the present invention provides an improved method of fitting a cochlear implant system to a patient by applying stimuli to multiple bands of electrodes, e.g., multiple groups of electrodes, while monitoring the stapedial reflex of the patient for the purpose of setting program parameters, e.g., T and M levels, for children or other patients who have a limited ability to report intensity information. More particularly, in one preferred embodiment, the present invention applies alternative stimuli, i.e., stimuli other than the constant amplitude stimuli used in prior fitting schemes, to multiple groups of electrodes in combination with detection of a desired stapedial reflex response, to quickly and accurately determine effective "T" and "M" levels that are more representative of "live speech". The use of such alternative stimuli by the present invention advantageously allows the entire fitting process to be completed in a very short time period, and generally eliminates the need for secondary adjustments.

Figure 3:
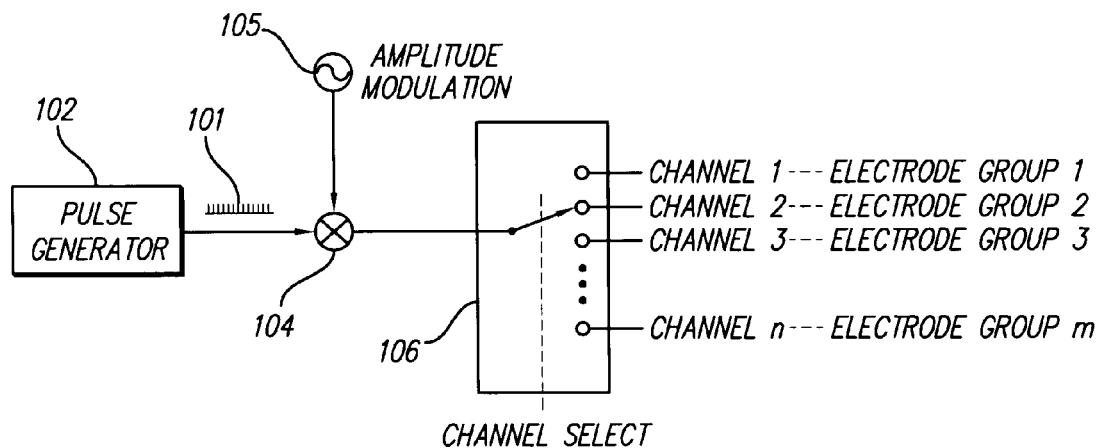
FIG. 3 illustrates application of speech-like stimuli, e.g., an amplitude modulated high rate pulsitile waveform, to multiple electrodes during the fitting process of a cochlear implant system.

For example, as shown in FIG. 3, one embodiment of the present invention generates modulated pulse trains with selectable degrees of amplitude modulation. In one variation of this embodiment, such modulated pulse trains may comprise internally-generated white noise. The amplitude modulated pulse trains are delivered to the speech processor during the fitting process on a channel-by-channel basis, and these channels are linked to selected groups of electrodes. Such modulated pulse trains better mimic the time varying nature of speech stimuli so that when combined with monitoring the stapedial reflex of the patient, a more accurate and effective stimulation intensity contour can be obtained for use by the implant system than has heretofore been possible.

Thus, as seen in FIG. 3, a pulse generator 102 generates a stream of pulses 101. The frequency of such stream of pulses 101 is preferably greater than about 2 KHz. e.g., with a period T less than about 500 microseconds (μS). The pulse width, PW, is relatively narrow, e.g., from about 11 μS to about 75 μS, but preferably around 21 μS. Such pulses 101 are then amplitude modulated in a modulator 104 with a selected modulation signal 105, e.g., a signal that provides speech-like stimuli, to produce an amplitude modulated stream of pulses 103. The amplitude modulated stream of pulses 103 is then applied, on a channel-by-channel basis through an appropriate multiplexer 106, or equivalent, to the inputs of the respective channels. The channels are linked to selected groups of electrodes. The intensity of the applied stream of pulses, e.g., the RMS amplitude, the average amplitude, the mean amplitude, the peak value, or other measure of the intensity of the modulated stream of pulses, is then varied as the stream of pulses is applied to a given group of electrodes until a desired stapedial reflex is detected or observed. This process is repeated for each group of a desired set of groups of electrodes, thereby defining a contour of threshold intensity levels for all of the electrodes. A final check of the contour thus obtained may be made by globally adjusting the contour to the observed or detected stapedial reflex, thereby providing a stimulation intensity for use by the implant system that more closely resembles actual "live speech".

The modulation signal 105 may take many forms, as described, e.g., in co-pending application Ser. No. 10/651,653, filed Aug. 29, 2003, incorporated herein by reference. In one embodiment, for example, the modulation signal mimics various speech-like stimuli. Such speech-like stimuli may include, for example, the following stimuli:

1. Shaped bands of noise whose overall bandwidth is adjustable. These bands are externally inputted in to the auxiliary input port 17 of the cochlear speech processor 16 at levels following the long-term spectrum of speech in each band. For example, shaped bands of noise may be used that cover the input center frequencies of 1, 3, 5 or more channels.
2. Modulated bands of noise whose center frequencies are adjustable.
3. Complex tonal stimuli whose spectra and various amplitude components are adjustable.
4. Speech tokens whose spectra and amplitude envelopes are well described.
5. White noise.

Figure 4A:
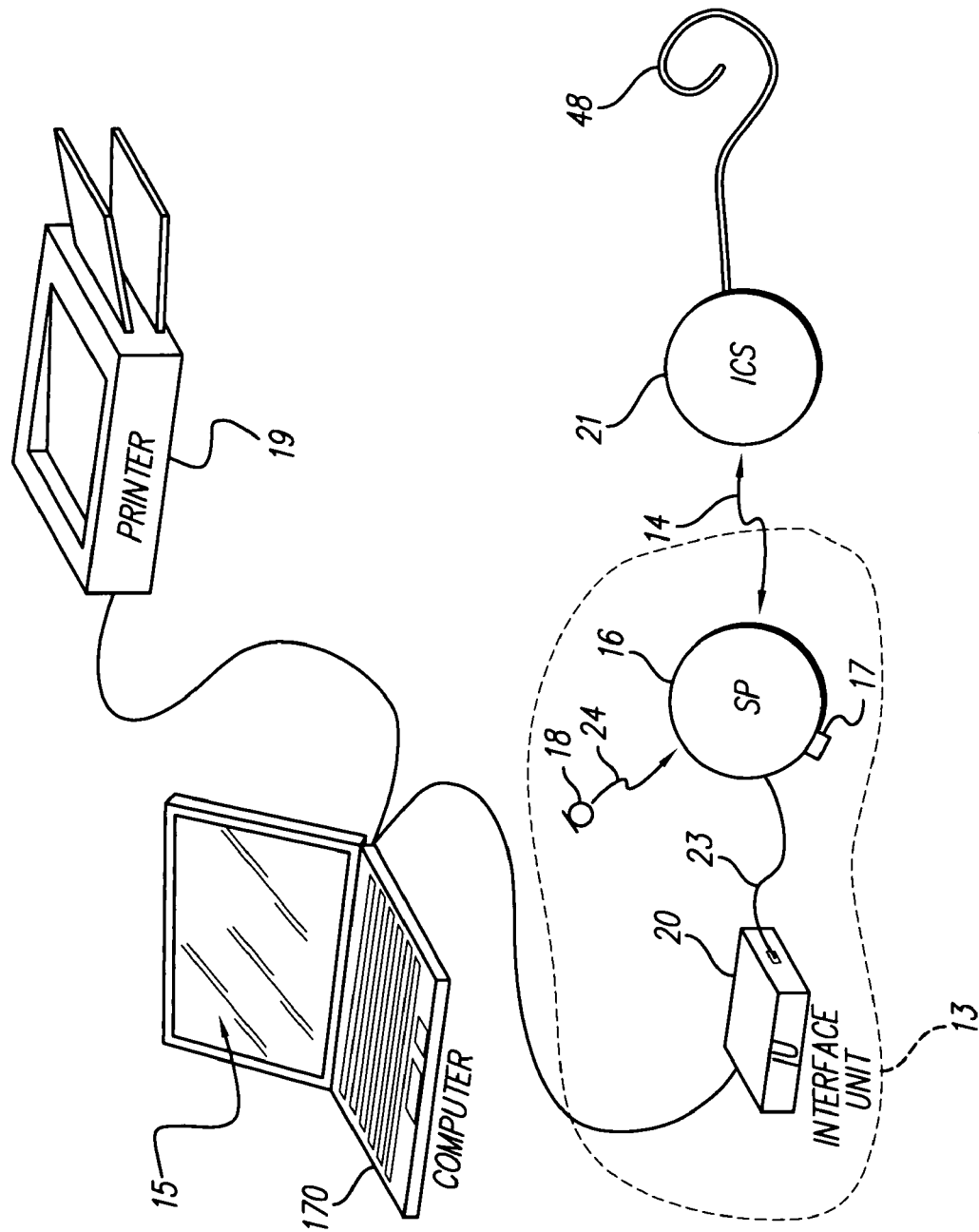
FIGS. 4A and 4B show respective fitting configurations that may be used during a fitting session.
Figure 4B:
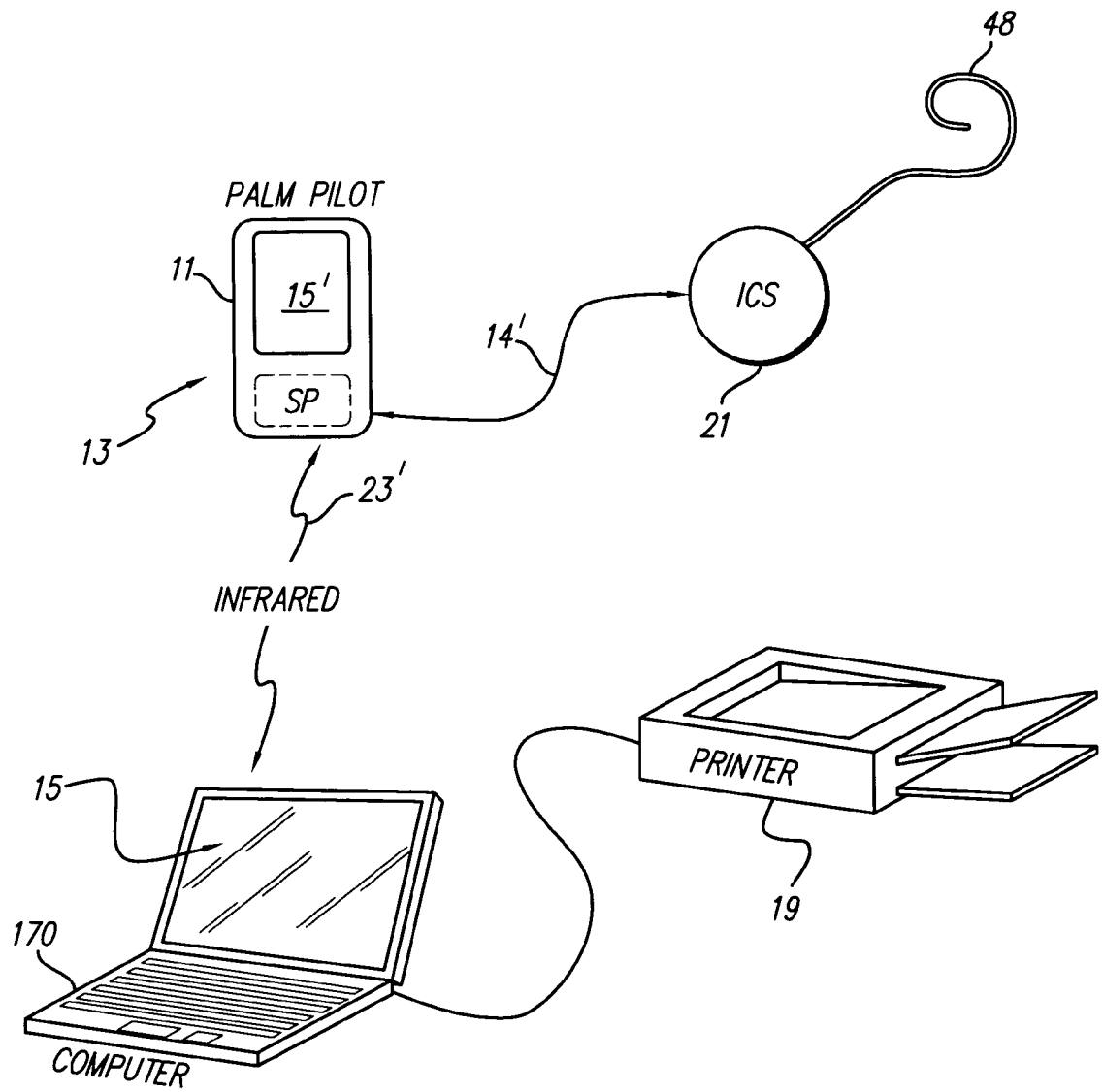

Representative fitting system configurations that may be used with the invention are illustrated in FIGS. 4A and 4B. The method of the present invention may be used with either of these fitting configurations, or other configurations.

As seen in FIG. 4A, there is shown a block diagram of the basic components used to fit a given patient with a cochlear implant system. As seen in FIG. 4A, the implant system is as shown in FIG. 1, and includes the SP 16 linked to an ICS 21 with electrode array 48. A microphone 18 is also linked to the SP 16 through a suitable communication link 24. A laptop computer 170, or other type of computer, or equivalent device, is coupled to the speech processor 16 through an interface unit (IU) 20, or equivalent device. The type of linkage 23 established between the IU 20 and the SP 16 will vary depending upon whether the SP 16 is implanted or not. Any suitable communications link 23 may be used, as is known in the art, and thus the details of the link 23 are not important for purposes of the present invention. It should be noted that for some applications, the IU 20 may be included within the computer 170 (e.g., as a communications interface already present within the computer, e.g., a serial port, or other built-in port, e.g., an IR port).

The computer 170, with or without the IU 20, provides input signals to the SP 16 that simulate acoustical signals sensed by the microphone 18, or received through the auxiliary input port 17, and/or provide command signals to the SP 16. In some instances, e.g., when testing the patient's threshold levels, the signals generated by the computer 170 replace the signals normally sensed through the microphone 18. In other instances, e.g., when testing the patient's ability to comprehend speech, the signals generated by the computer 170 provide command signals that supplement the signals sensed through the microphone 18.

The laptop computer 170 (or equivalent device) provides a display screen 15 on which selection screens, stimulation templates and other information may be displayed and defined. Such computer 170 thus provides a very simple way for the audiologist or other medical personnel, or even the patient, to easily select and/or specify a particular pattern of stimulation parameters that may be thereafter used, even if for just a short testing period, regardless of whether such stimulation pattern is simple or complex. Also shown in FIG. 4A is a printer 19 which may be connected to the computer 170, if desired, in order to allow a record of the selection criteria, stimulation templates and pattern(s) that have been selected and/or specified to be printed.

FIG. 4B illustrates an alternative fitting system that may also be used. In FIG. 4B, the ICS 21 is linked to a speech processor configured or emulated within a palm personal computer (PPC) 11, such as a Palm Pilot, or equivalent processor, commercially available, e.g., from Hewlett Packard. Such PPC 11 includes its own display screen 15' on which some graphical and textual information may be displayed. In use, the PPC 11 is linked, e.g., through an infrared link 23', to another computer, 170, as necessary. Typically, the functions of the SP and related devices are stored in a flashcard (a removable memory card that may be loaded into the PPC 11), thereby enabling the PPC 11 to perform the same functions of those elements encircled by the dotted line 13 in FIG. 4A. The PPC 11 is coupled to the ICS 21 through a suitable data/power communications link 14'.

Figure 5:
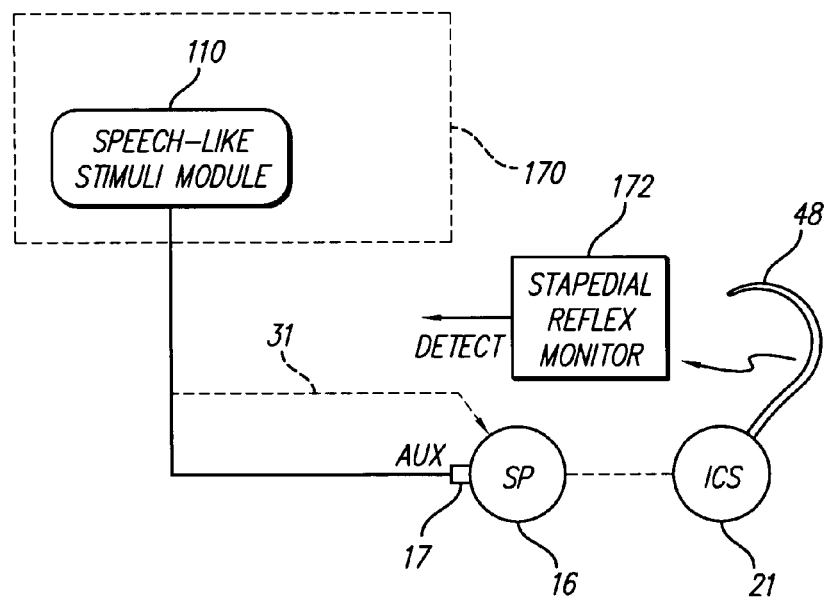
FIG. 5 illustrates application of speech-like stimuli to the speech processor of a cochlear implant system so that such stimuli are applied simultaneously to multiple channels of the implant system during a fitting session.

Advantageously, all of the stimuli used by the present invention during the sound processor setting procedure (or fitting process) may be generated through a software module 110 that is incorporated into the computer 170, or equivalent processor, as illustrated generally in FIG. 5. Moreover, as additionally illustrated in FIG. 5, and as a further simplification to the fitting process, the software module 110 may be linked directly to the auxiliary input port 17 of the speech processor 16, thereby eliminating the need for an interface unit 20, or equivalent device (see FIG. 4A). Alternatively, and as an additional simplification to the fitting process, the software module 110 may be included within (internal to) the speech processor 16, being linked to the appropriate signal processing paths within the speech processor through the signal injection line 31.

As seen in FIG. 5, once the stimuli generated by the module 110 are applied to the speech processor 16, the speech processor responds to such signals by generating appropriate stimuli that are coupled to the ICS 21 and applied to selected groups of electrodes within the electrode array 48. While such stimuli are thus being applied to the inner ear of the patient through the electrode array 48, the stapedial reflex of the patient is monitored through use of a stapedial reflex monitor 172. The monitor 172 may take many forms. For example, a traditional stapedial reflex monitor may be used that is based on direct observation or visual inspection, or that is based on a change in the impedance of the tympanic membrane. Alternatively, or conjunctively, a stapedial electrode may be implanted in the patient, as described, e.g., in U.S. Pat. No. 6,208,882, and the voltage developed on such electrode (resulting from depolarization of the stapedial muscle tissue) may be monitored by the monitor 172.

Figure 6:
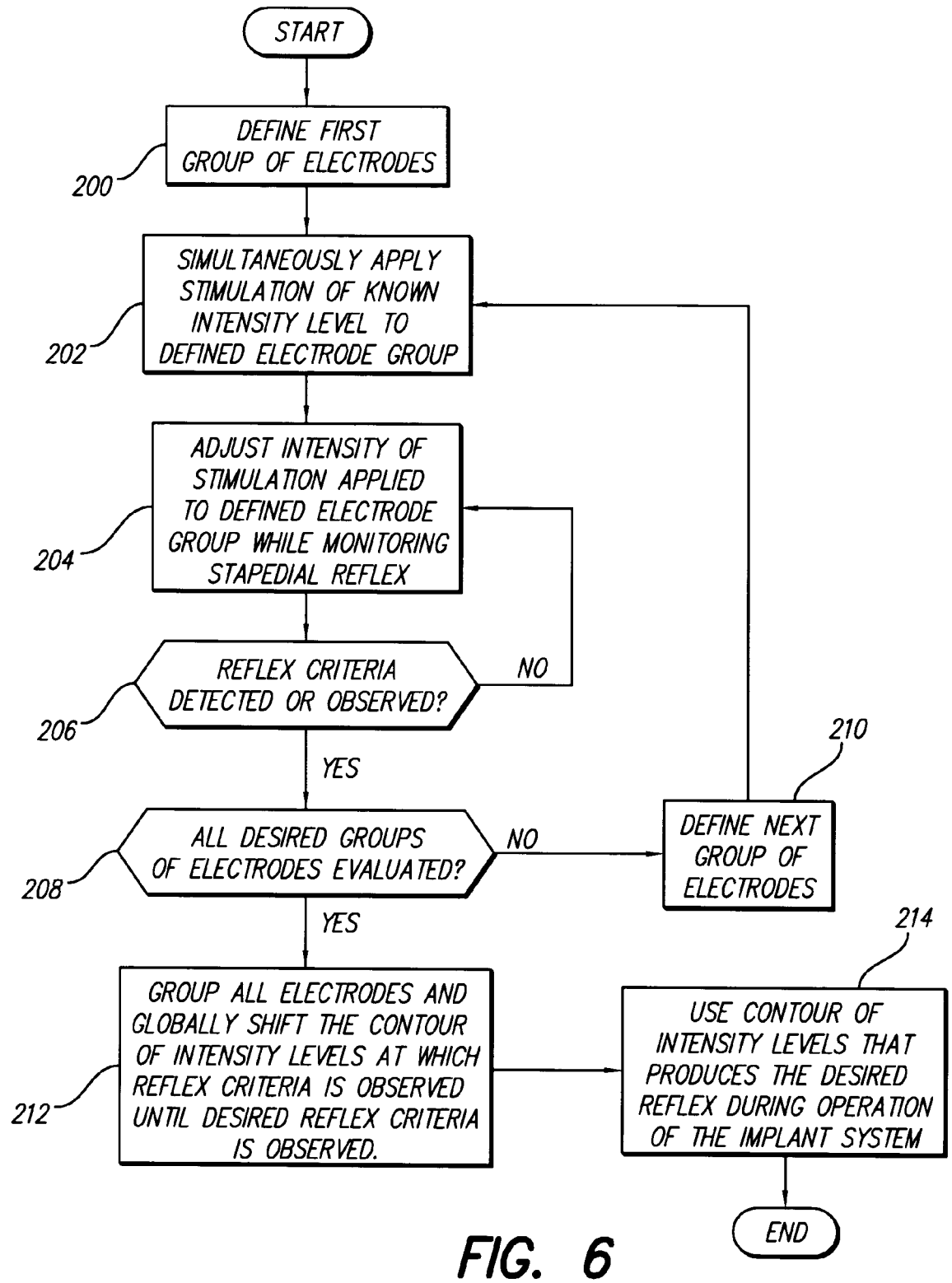
FIG. 6 is a flow chart that depicts the method of fitting of the present invention.

Next, with reference to FIG. 6, a flow chart is shown that illustrates the method of the invention, wherein the main steps of the invention are identified in "boxes" or "blocks" that interconnect to define a flow or sequence of steps. As seen in FIG. 6, the method begins by defining a first group of electrodes that are to receive stimuli at live speech rates (block 200). Once such group of electrodes is defined, the next step is to simultaneously apply stimuli at live speech rates, e.g., rates greater than about 2 KHZ, to the defined group of electrodes (block 202). It should be noted that as used here, "simultaneous" means perceived as being applied at the same time. As mentioned previously, such simultaneous perception will occur when the stimuli are applied at the same time to all electrodes, or may also occur when the stimuli are applied sequentially to the electrodes within the group at a rate sufficiently fast so that the stimulation is perceived as having occurred simultaneously.

The intensity of the applied stimuli is then adjusted, generally starting at a low level and gradually increasing to a high level, while the stapedial reflex of the patient is monitored (block 204). At some point, the stimulation applied to the group of electrodes will evoke a response from the patient that is detectable by the stapedial reflex. Hence, for each applied stimuli intensity, a determination is made whether a reflex criteria occurs (block 206). If no reflex is observed that meets the defined criterion (NO branch of block 206), then further adjustment of the stimuli intensity continues (block 204). If a reflex is observed (YES branch of block 206), then the intensity level of the stimuli applied to that group of electrodes represents a potential threshold data point on a contour of threshold data points that may be used by the implant system to control the intensity of the stimuli that will be applied to the patient during normal operation of the system.

Once a reflex criteria has been observed for a group of electrodes, then a determination is made as to whether all of the desired electrode groups have been evaluated (block 208). If not (NO branch of block 208), then the next electrode group is defined (block 210), and the process repeats itself for that next group of electrodes (blocks 202, 204, 206). If all the electrode groups have been evaluated (YES branch of block 208), then that means the contour of threshold data points for all desired groups of electrodes has been completed. While such contour of threshold values could then be used to set the operating parameters of the implant system, the method is further enhanced by grouping all of the electrodes into a single group, i.e., applying the stimuli to a group of electrodes that includes all of the electrodes, and globally shifting the contour of threshold values previously determined until a desired reflex criteria is observed (block 212). At that point, the globally-adjusted or globally-shifted contour of intensity levels that produces the desired stapedial reflex may be used during operation of the implant system to provide the patient with threshold levels that more closely resemble actual "live speech" (block 214).

By way of example, assume that a cochlear implant system, such as the CLARION cochlear implant system available from Advanced Bionics Corporation, has 16 electrodes, identified as electrodes E1, E2, E3, . . . E16. As a first step, electrodes E1–E4 are grouped together, and stimuli are applied simultaneously to electrodes E1–E4, while gradually increasing the intensity of the stimuli, until a reflex criterion is observed. Next, as a second step, electrodes E5–E8 are grouped together, and stimuli are applied simultaneously to electrodes E5–E8, while gradually increasing the intensity of the stimuli, until a reflex criterion is again observed. Similarly, as a third step, electrodes E9–E12 are grouped together, and stimuli are applied simultaneously to electrodes E9–E12, while gradually increasing the intensity of the stimuli, until the desired reflex criterion is observed. Then, as a fourth step, electrodes E13–E16 are grouped together, and stimuli are applied simultaneously to electrodes E13–E16, while gradually increasing the intensity of the stimuli, until the desired reflex criterion is observed. Lastly, as a fifth step, all of the electrodes E1–E16 are grouped together, and the contour obtained during steps one through four is globally shifted by gradually increasing or decreasing the intensity of the stimuli applied to the E1–E16 group until the reflex criteria is observed.

As the above example illustrates, a five step process may be used to set the threshold levels needed by the system during operation. Smaller or larger groups of the electrodes could be used depending upon how much time is available for completing the fitting process. The stimulus is applied sequentially or simultaneously at the pulse rate of the "live-speech" program to each of the electrode contacts in the group. The stimulus may be modulated or unmodulated, and its duration (pulse width) may be controllable by the software module 110 (FIG. 5), or equivalent pulse generator.

As described above, it is thus seen that the invention provides an improved method of fitting a multichannel cochlear implant system that uses the stapedial reflex of the patient and multiband stimulation to better determine effective intensity threshold levels, e.g., T and M levels, used by the implant system during its operation.

As further described above, it is seen that the invention provides an improved method of fitting that does not require subjective feedback from the patient during the fitting procedure.

While the invention herein disclosed has been described by means of specific embodiments and applications thereof, numerous modifications and variations could be made thereto by those skilled in the art without departing from the scope of the invention set forth in the claims.

What is claimed is:

1. In a cochlear implant system having a sound processor and multiple electrode contacts through which stimuli are adapted to be applied to a patient's inner ear, a method of "fitting" the cochlear implant system to the patient, comprising:
   identifying multiple groups of the electrode contacts;
   applying electrical stimuli to all of the electrode contacts of select groups of the electrode contacts and monitoring stapedial reflexes of the patient such that temporal and spatial integration during live speech are accounted for and the accuracy of predicting live speech comfort levels is increased; and
   using the stapedial reflexes to control the intensity of electrical stimuli thereafter applied through the electrode contacts by the cochlear implant system.

2. The method of claim 1, further including:
   forming a contour of intensity levels associated with all of the select groups of electrode contacts at which a reflex criteria of the stapedial reflex responsive to the delivered electrical stimuli is first observed.

3. The method of claim 1, wherein applying electrical stimuli includes applying pulse trains of electrical stimuli with selectable degrees of intensity.

4. The method of claim 3, further including modulating the amplitude of the pulse trains of electrical stimuli.

5. The method of claim 3, wherein the pulse trains of electrical stimuli are derived from shaped bands of noise whose overall bandwidth is adjustable.

6. The method of claim 3, wherein the pulse trains of electrical stimuli are derived from modulated bands of noise whose center frequencies are adjustable.

7. The method of claim 3, wherein the pulse trains of electrical stimuli are derived from complex tonal stimuli whose spectra and various amplitude components are adjustable.

8. The method of claim 3, wherein the pulse trains of electrical stimuli are derived from speech tokens using spectra and amplitude envelopes.

9. The method of claim 3, wherein the pulse trains of electrical stimuli are derived from white noise.

10. The method of claim 1, wherein applying electrical stimuli includes applying an amplitude modulated pulse train at a known intensity level and having a rate of at least 2 kHz.

11. In a cochlear implant system having a sound processor and multiple electrode contacts through which stimuli are adapted to be applied to a patient's inner ear, a method of "fitting" the cochlear implant system to the patient, comprising:

identifying multiple bands of the electrode contacts, each band including three or more adjacent electrode contacts;

applying electrical stimuli to all of the electrode contacts of select bands of the electrode contacts and monitoring stapedial reflexes of the patient; and using the stapedial reflexes to control the intensity of electrical stimuli thereafter applied through the electrode contacts by the cochlear implant system.

12. The method of claim 11, further including:

forming a contour of intensity levels associated with all of the select bands of electrode contacts at which a reflex criteria of the stapedial reflex responsive to the delivered electrical stimuli is first observed.

13. The method of claim 11, wherein applying electrical stimuli includes applying pulse trains of electrical stimuli with selectable degrees of intensity.

14. The method of claim 13, further including modulating the amplitude of the pulse trains of electrical stimuli.

15. The method of claim 13, wherein the pulse trains of electrical stimuli are derived from shaped bands of noise whose overall bandwidth is adjustable.

16. The method of claim 13, wherein the pulse trains of electrical stimuli are derived from modulated bands of noise whose center frequencies are adjustable.

17. The method of claim 13, wherein the pulse trains of electrical stimuli are derived from complex tonal stimuli whose spectra and various amplitude components are adjustable.

18. The method of claim 13, wherein the pulse trains of electrical stimuli are derived from speech tokens using spectra and amplitude envelopes.

19. The method of claim 13, wherein the pulse trains of electrical stimuli are derived from white noise.

20. The method of claim 11, wherein applying electrical stimuli includes applying an amplitude modulated pulse train at a known intensity level and having a rate of at least 2 kHz.

* * * * *